United States Patent
Jeng et al.

(10) Patent No.: US 7,116,814 B2
(45) Date of Patent: Oct. 3, 2006

(54) IMAGE-BASED CONTAINER DEFECTS DETECTOR

(75) Inventors: Bor-Shenn Jeng, Taoyuan (TW); Quen-Zong Wu, Taoyuan (TW); Yu-Pin Chen, Taoyuan (TW); Wei-Yuan Cheng, Taoyuan (TW)

(73) Assignee: Chunghwa Telecom Co., Ltd., Taoyuan (TW)

( * ) Notice: Subject to any disclaimer, the term of this patent is extended or adjusted under 35 U.S.C. 154(b) by 740 days.

(21) Appl. No.: 10/256,008

(22) Filed: Sep. 27, 2002

(65) Prior Publication Data

US 2004/0062348 A1    Apr. 1, 2004

(51) Int. Cl.
*G06K 9/00* (2006.01)
(52) U.S. Cl. ............... 382/141; 382/142; 382/143; 382/144; 382/145; 382/147; 382/149
(58) Field of Classification Search ............... 382/254, 382/255, 260–265, 269, 274, 275, 141–147
See application file for complete search history.

(56) References Cited

U.S. PATENT DOCUMENTS

| | | | |
|---|---|---|---|
| 6,377,698 B1 * | 4/2002 | Cumoli et al. ............ 382/101 |
| 6,453,067 B1 * | 9/2002 | Morgan et al. ............ 382/162 |
| 6,647,132 B1 * | 11/2003 | Montillo et al. ............ 382/106 |
| 6,763,148 B1 * | 7/2004 | Sternberg et al. ............ 382/293 |

* cited by examiner

*Primary Examiner*—Jingge Wu
*Assistant Examiner*—Brian Le
(74) *Attorney, Agent, or Firm*—Rabin & Berdo, P.C.

(57) ABSTRACT

The image-based container defects detector consists of a plurality of camera units, a sensor unit, a frame grabber, and an image recognizer unit. The sensor unit serves to detect the vehicles entering the inspection station, and transmit a signal to the frame grabber for capturing the vehicle image by triggering the CCD camera thereby obtaining the information about the container's defect position and size. By dexterously utilizing image processing technique, the HIS (hue, saturation and intensity) color is employed to distinguish a normal area from a defected area in the container. Then quad-tree and merge is used to segregate image roughly. As for the non-defected area becoming obscured due to noise is removed using a filter. Finally the defected area is displayed on the screen. The present invention is well-suited for after detection as well as for on-line immediate detection for defect containers.

2 Claims, 6 Drawing Sheets

IMAGE-BASED CONTAINER DEFECTS DETECTOR

BACKGROUND OF THE INVENTION

1. Field of the Invention

The present invention relates to an image-based container defects detector, and more particularly, to an image based container detector applicable in a container yard, or an inspecting station to detect the position and size of the container defect in the crucial time. If it is in combined use with the container number recognizer, it can improve efficiency and capacity of freight handling and contribute to automation of freight handling in the container yard.

2. Description of the Prior Art

Up to now, the way for finding out container defects is inspecting the container outer appearance by visual observation to record the defected positions and their sizes on the paper. But in this manual approach it is unable to find out defects in crutial time. It also causes potential danger and wasting time and manpower for the worker to work by foot for inspecting containers one by one.

In general, the procedure for conventional image-based container defects detector is at first to prepare the original container image, and then to find out the defects by subtracting the backround image from the newly captured image. Should the difference be exceeding a prescribed value, it is judged abnormal. Since the distance from the CCD camera to the container in the captured image is not equal to that in the original background image, or by extra interference arising from the container's dirts or background noise, the aforementioned difference will be too large to obtain an allowable recognition precisement.

Meanwhile, being affected by light sources, the color rendering of the dark background image obtained thereof will not be appreciable.

In view of the foregoing situation, the inventors of the invention herein conducted intensive research based on many years of experience gained through professional engagement in this field, with continuous experimentation and improvement culminating in the development of this dexterous image-based container defects detector.

SUMMARY OF THE INVENTION

The main object of the present invention is to provide an image-based container defects detector applicable in a container yard, or an inspection station to detect the position and size of the container defect in the crucial time, and advantageously in combined use with the container number recognizer so as to improve efficiency and capacity of freight handling and contribute to automation of freight handling.

To achieve the above mentioned objects, the image-based container defects detector of the present invention consists of a plurality of camera units, a sensor unit, a frame grabber, and an image recognizer unit. The sensor unit serves to detect the vehicles entering the inspection station, and transmit a signal to the image frame grabber for taking the vebicle image by triggering the CCD camera thereby obtaining the information about the container's defect position and size. By dexterously utilizing image processing technique, the HIS (hue, saturation and intensity) color is employed to distinquish a normal area from a defect area in the container. Then quad-tree and merge is used to segregate image roughly. As for the non-defected area becoming obscured from noise is removed using a filter. Finally the defected area is displayed on the screen. The present invention is well-suited for after detection as well as for on-line immediate detection for containers.

BRIEF DESCRIPTION OF THE DRAWINGS

For fuller understanding of the nature and objects of the invention, reference should be made to the following detailed description taken in conjunction with the accompanying drawings in which.

DETAILED DESCRIPTION OF THE PREFERRED EMBODIMENT

Figure 1:
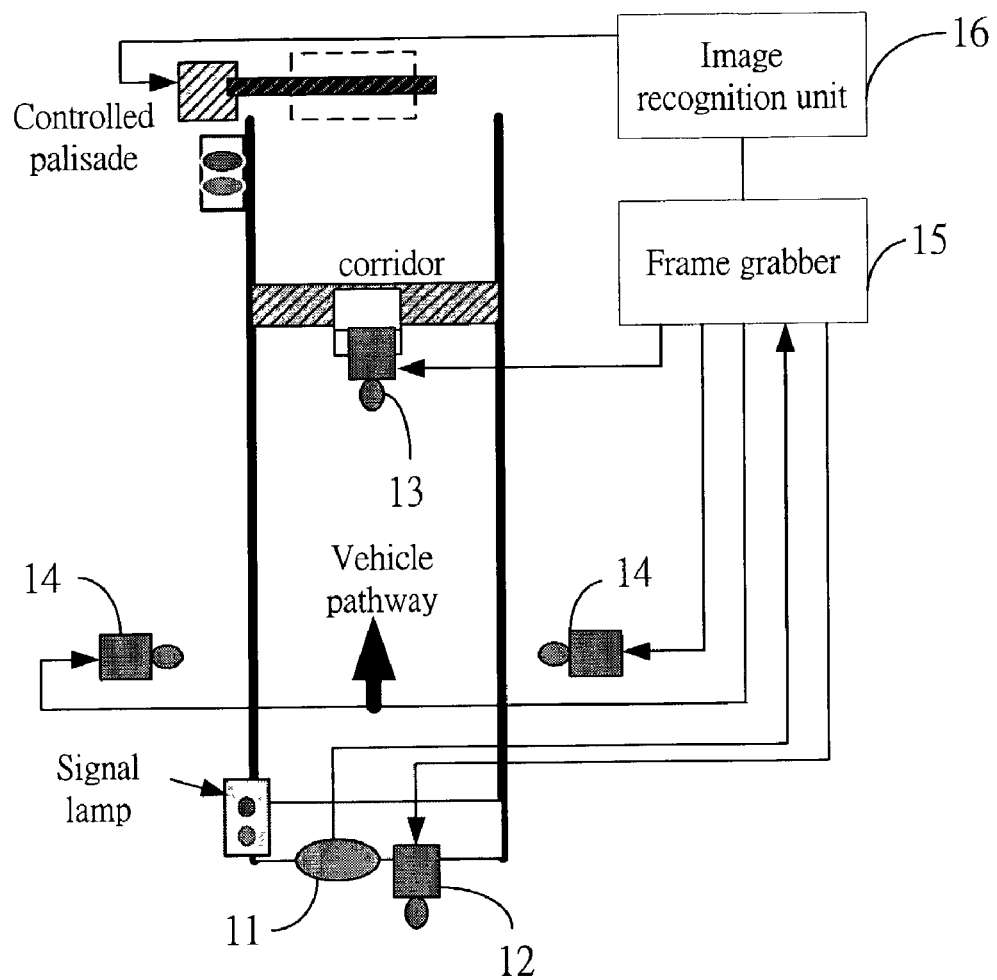
FIG. 1 is the layout diagram of the image-based container defects detector according to the present invention.
Figure 1:
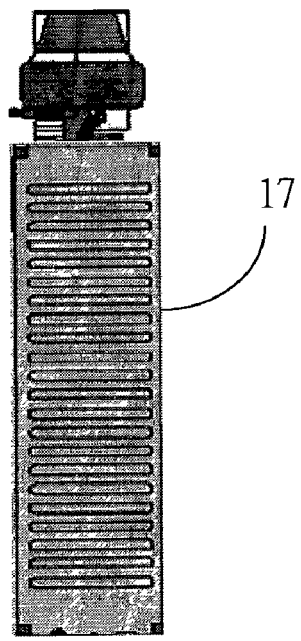

Referring to FIG. 1, the layout diagram of the image-based container defect detector, the system consists of an induction unit 11, a front CCD camera 12, a rear CCD camera 13, a side CCD camera 14, an image frame grabber 15, and an image recognition unit 16. Wherein the induction unit 11 detects the container car 17 entering the inspection station, and sends the signal to the image frame grabber 15 for triggering the front CCD camera 12, rear CCD camera 13, and the side CCD camera 14 to capture a container image card from three direction. The induction unit 11 may be a reflection, or a direct aiming or a loop sensor to detect the object in the induction area. If a container car enters the induction area (inspection station), the induction unit 11 actuates the frame grabber 15 to trigger the camera for capturing an image (front, rear, or side) of the car. Then the captured image is transferred to the image recognition unit 16 to identify the container number.

The image recognition unit 16 is the kernel of the present invention. It serves to detect the position and size of the defects using image process technique from any one of the image cards captured by CCD cameras 13, 14 and 15.

Figure 2A:
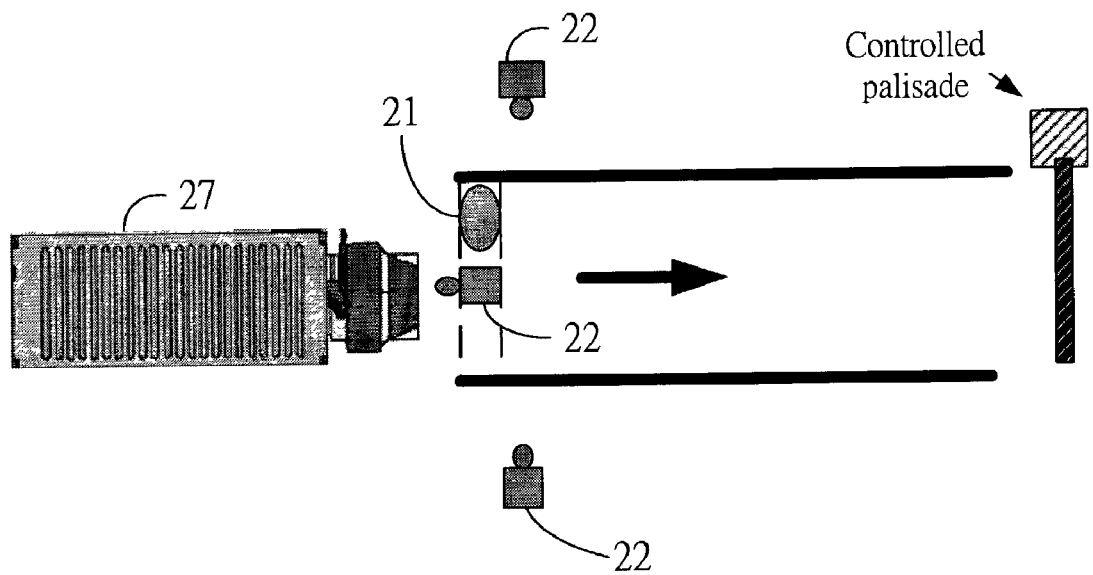
FIGS. 2A and 2B are the layout diagrams of the present invention for a single container defects detection.
Figure 2B:
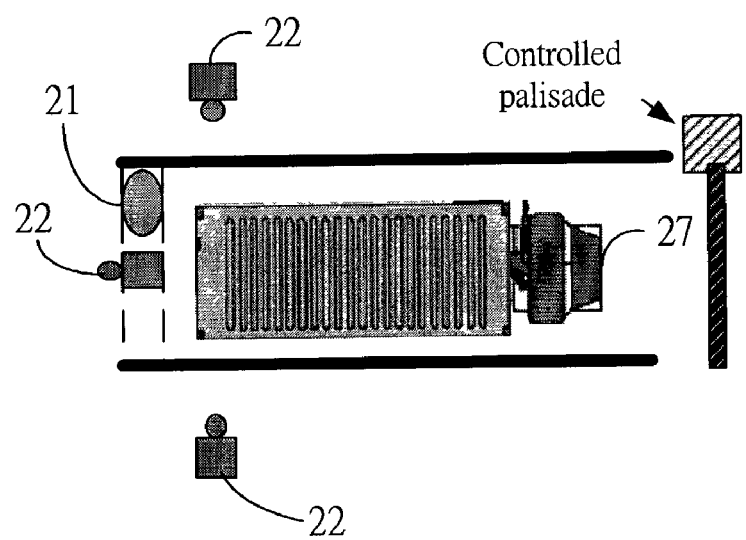

FIGS. 2A and 2B are the layout diagrams of the image-based container defects detector of the present invention for a single container defects detection. As shown in these two figures, an induction unit 21 serves to detect a container car 27 entering the inspection area. As soon as the induction unit 21 has detected the front part of the coning container car 27, a signal is transmitted to the frame grabber 15 to trigger a CCD camera 22 to capture a front (snapped from the right side of the car) cotainer image; in the meanwhile, when the induction unit 21 has detected the rear part of the leaving container car, a signal is transmitted to the frame grabber 15 to trigger the CCD camera 22 to capture a rear image. (snapped from the left side of the car). Here the induction unit 21 may be a reflection, or a direct aiming, or a loop sensor to detect the object in the induction area. Then the captured images are transferred to the image recognition unit 16 to identify the container number and find out the defects.

Figure 3A:
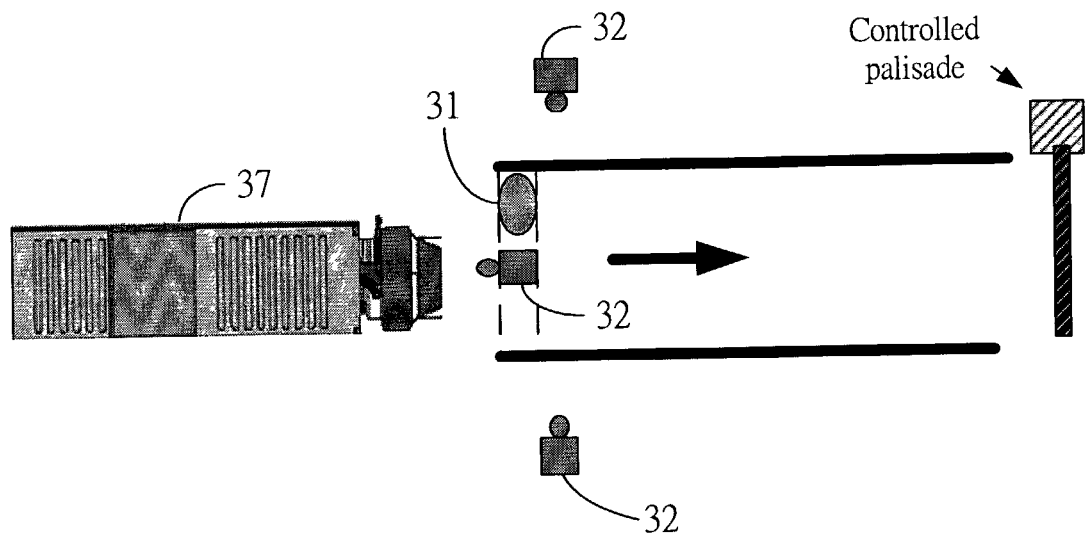
FIGS. 3A and 3B are the layout diagrams of the present invention for double containers defects detection.
Figure 3B:
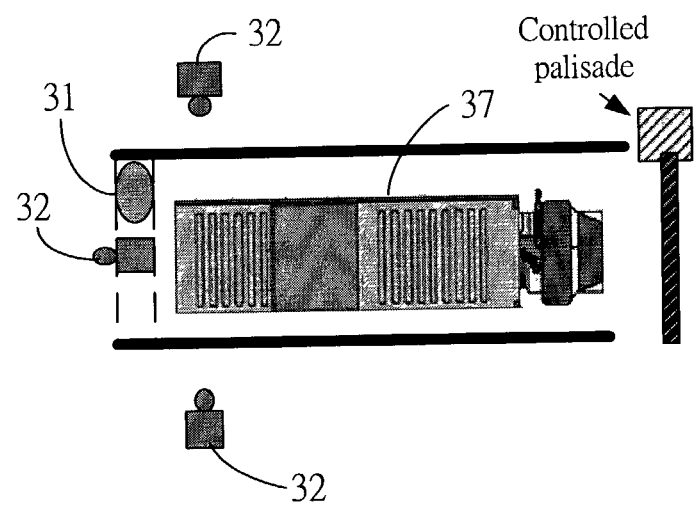

FIGS. 3A and 3B are the layout diagrams of the image-based container defects detector of the present invention for double containers defects detection. As shown in these two figures, an induction unit 31 serves to detect a container car 27 entering the inspection area. As soon as the induction unit 31 has detected the front part of the first container a signal is transmitted to the frame grabber 15 to trigger a CCD camera 32 to capture a front (snapped from the right side of the car) image of the first container, in the meanwhile, when the induction unit 31 has detected the rear part of the first container, a signal is transmitted to the frame grabber 15 to trigger the CCD camera 32 to capture a rear image (snapped from the left side of the car). In the similar way, as soon as the induction unit 31 has detected the front part of the second container, a signal is transmitted to the frame grabber 15 to trigger the CCD camera 32 to capture a front (snapped from the right side of the car) image of the second container; in the meanwhile, when the induction unit 31 has detected the rear part of the second container, a signal is transmitted to the grabber 15 to trigger the CCD camera 32 to capture a rear image (snapped from the left side of the car). Here, the induction unit 31 may be a reflection, or a direct aiming, or a loop sensor to detect the object in the induction area. Then the captured images are transferred to the image recognition unit 16 to identify the container number and find out the defects.

Figure 4:
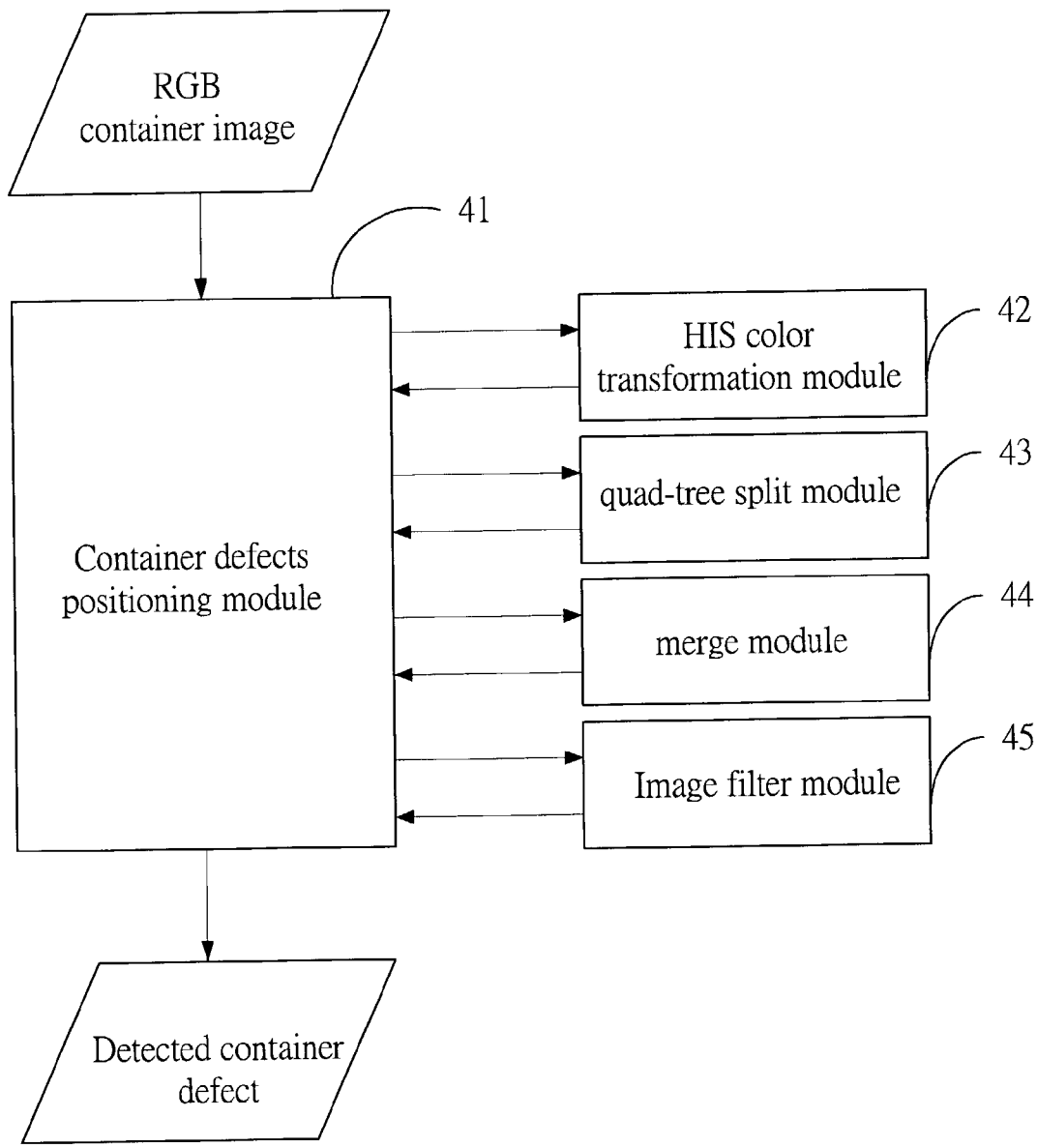
FIG. 4 is the flowchart of the image-based container defects detector according to the present invention.

FIG. 4 is the flowchart of the image-based container defects detector according to the present invention. In this flowchart, the system is composed of program modules including a HIS color transformation module 42, a quad-tree split module 43, an image merge module 44, and an image filter module 45. When a container image is inputted, at first a container defect positioning program module 41 works to look for possible location, then capture an image of the container number area, this image is then segmented from the normal image roughly employing the quad-tree spit module 43 and the image merge module 44 after its HIS color is transformed by the HIS color transformation module 42. After segmentation, the normal image is filtered out by the image filter module 45. Finally, the segmented defect position is further precisely located by a container defect positioning module 41 according to the segregated segment.

Figure 5:
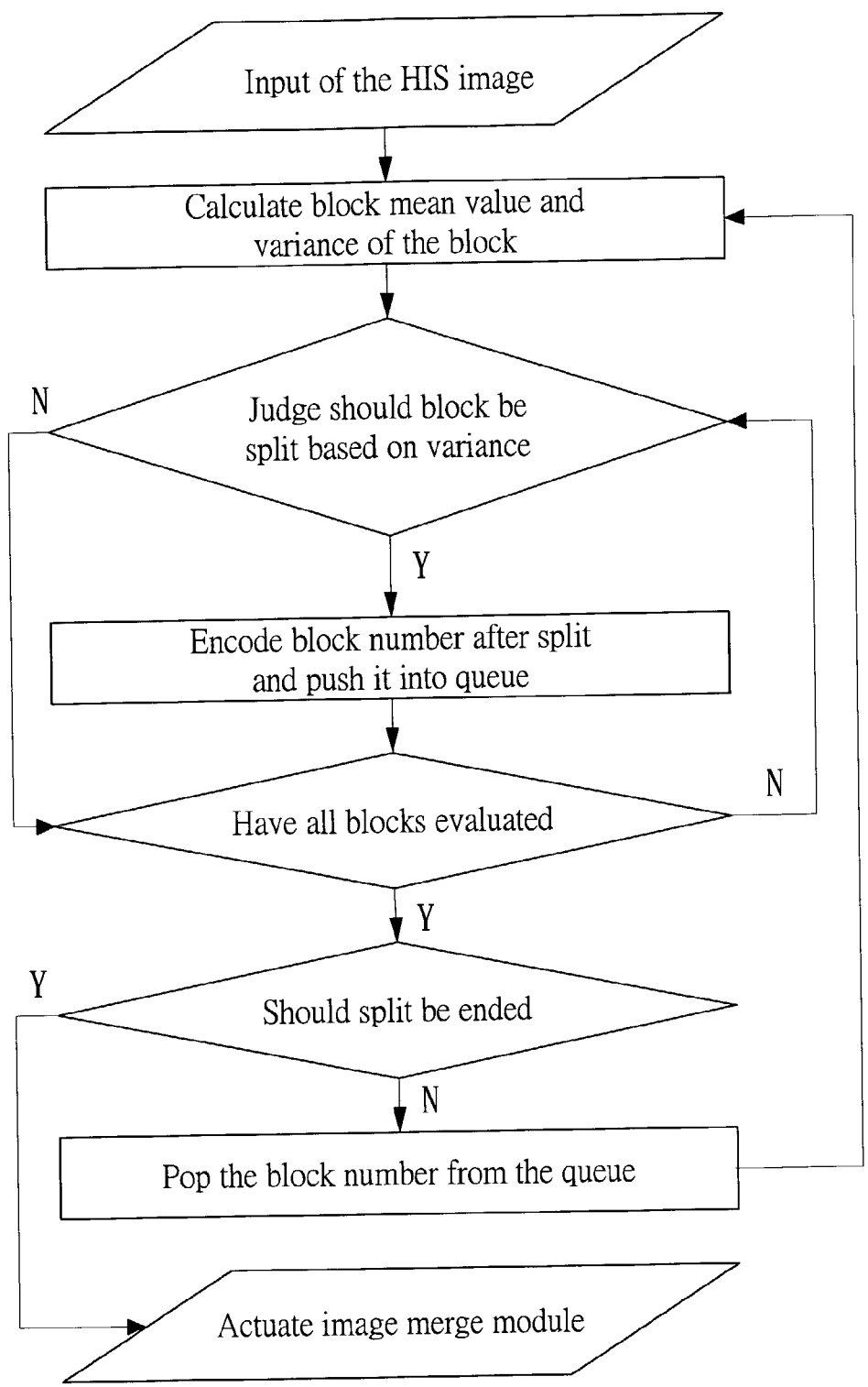
FIG. 5 is the flowchart of the quad-tree split module according to the present invention.

For fuller illustration of function of each program module, at first referring to FIG. 5 in which the flowchart of the quad-tree split module is shown. The image is segmented into 20×15 blocks, and the block size is 32×32. Then each block is split by quad-tree module respectively. For simplifying in writing a program. The block is encoded in the way defining the left-top area in the block being number 1, the right-top area in the block being number 2, the left-bottom area in the block being number 3, and the right-bottom area being number 4. Similarly, we define the left-top area in the sub-block being number 11, the right-top area in the sub-block being number 12, the left-bottom area in the sub-block being number 13, and the right-bottom area in the sub-block being number 14 and so on. Besides, the code number is pushed into queue for each split block. After completion of the above process, each code umber is taken out from queue and checked whether it is necessary to split again until there is no code number in queue.

The split process is thus completed.

The process of merge module is carried out as follows:

Algorithm: Merge

Input: The image input after split

Output: The image output after segmentation

Procedure:

Initialization of each block to a unique level

Do

```
Change = false
for top to bottom
    for top to bottom
        for left to right
            if (8-Neighbors have different label)
                judge if merge is necessary according to mean
                if (mean < = threshold
                MIN(label of block to merge)
                calculate the mean of the block again
                change = true
                end if
            end if
        end for
    end for
for top to bottom
    for top to bottom
        for left to right
            if (8-Neighbors have different label)
                judge if merge is necessary according to mean
                if (mean <= threshold
                MIN(label of block to merge )
                calculate the mean of the block again
                change = true
                end if
            end if
        end for
    end for
until change = false
```

This algorithm is similar as connected component labeling algorithm. First, each segmented block is assigned a unique label, and is scanned from left to right and from top to bottom for mean HIS color value of each of 8-neighbors. If mean values of neighboring blocks are similar, set these neighboring blocks as the minimal label of 8-neighboring blocks. Iteratively carry this process from right to left and from bottom to top and so on for several rounds, merged and labeled image can be obtained.

Figure 6:
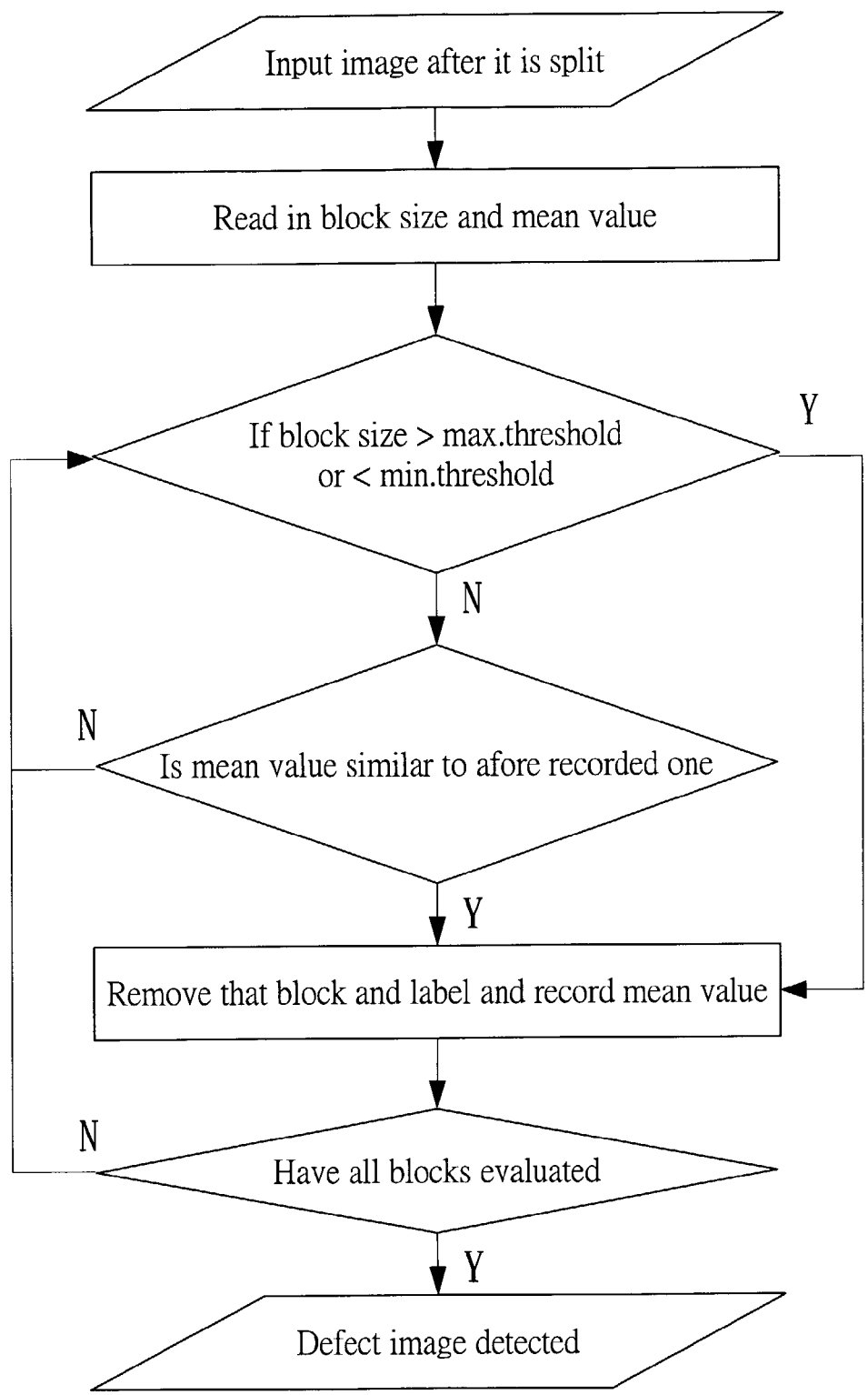
FIG. 6 is the flowchart of filter module according to the present invention.

FIG. 6 is the flow chart of the filter module according to the present invention. It is assumed the larger area must be the background of the container and the smaller area must be that caused by noise. Besides, the colors of defected region and non-defected region are different. Hence, a filter can be used to remove these areas using a threshold based on color and size of the region. Further to this, since the contaminated region of the container is discontinued, the record of mean value can helps to eliminate these areas.

It emerges from the description of the above examples that the invention has several noteworthy advantages, in particular:

(1) Combined application of quad-tree split and merge modules to segment the container image and analization of difference between segmented areas eliminates possible errors caused by noise including reflected light or shadow thereby the reliability of detected results is high.

(2) Use of variance computation in split module leads to better inspection result than that obtained by conventional grey Max-Min grade comparison.

(3) Light sources influence such as variation of light intensity and reflexion of light is not serious to the system wherein HIS color transformation module is used.

(4) Utilization of the quad-tree data structure can accelerate the speed of the split module.

(5) Utilization of the modified connected components labeling algorithm results in obtaining better merged images.

(6) By utilization of Mean value recording structure, the discontinuity of dirts contaminated segments can be recombined so as to upgrade the detection precisement.

Although the invention has been described in terms of preferred embodiments, it is apparent that numberous variations and modifications may be made without departing from the true spirit and scope thereof, as set forth in the following claims.

What is claimed is:

1. An image-based container defects detector for finding a defect located in a defective portion of a container that also has a normal portion that is not defective, the container additionally having a container number in a container number area, said defect detector comprising:

container defect positioning program module means for capturing the container number area in a colored image of the container;

HIS (Hue, Intensity, Saturation) color transformation module means for transforming the image in color to provide a transformed image;

segmentation means for receiving the transformed image and segmenting the defective portion form the normal portion to provide a segmented image, the segmentation means including a quad-tree split module and an image merge module;

image filter module means for filtering the normal portion out of the segmented image to provide a filtered image; and container defect positioning module means for precisely locating the defect in the segmented image, wherein the quad-tree split module segments the transformed image into 20×15 blocks of size 32×32 and then the blocks are selectively split by said quad-tree module into sub-blocks, wherein the quad-tree split module utilizes HIS color variance to determine whether blocks should be split, wherein a code number is given to each sub-block and the code number is pushed into a queue, and wherein each code number is taken out of the queue and checked should the corresponding sub-block should be split again.

2. A image-based container defects detector for finding a defect located in a defective portion of a container that also has a normal portion that is not defective, the container additionally having a container number in a container number area, said defect detector comprising:

container defect positioning program module means for capturing the container number area in a colored image of the container;

HIS (Hue, Intensity, Saturation) color transformation module means for transforming the image in color to provide a transformed image;

segmentation means for receiving the transformed image and segmenting the defective portion form the normal portion to provide a segmented image, the segmentation means including a quad-tree split module and an image merge module;

image filter module means for filtering the normal portion out of the segmented image to provide a filtered image; and container defect positioning module means for precisely locating the defect in the segmented image, wherein the segmented image has a plurality of blocks, wherein the image merge module assigns each block a unique level, and scans from left to right, and from top to bottom for a mean HIS color value of each of 8 neighboring blocks in a first procedure, wherein if mean values of neighboring blocks are similar, these neighboring blocks are set as a minimal label among 8 neighboring blocks in a second procedure, and wherein the first and second procedures are repeated iteratively, from right to left and from bottom to top, for several rounds so as to obtain a merged and labeled image.

* * * * *